United States Patent [19]
Barnhart

[11] Patent Number: 6,053,925
[45] Date of Patent: Apr. 25, 2000

[54] LESION LOCALIZATION DEVICE AND METHOD

[76] Inventor: William H. Barnhart, 1516 California Ave., Iowa City, Iowa 52240

[21] Appl. No.: 09/032,720

[22] Filed: Feb. 27, 1998

[51] Int. Cl.[7] .................................................. A61B 17/34
[52] U.S. Cl. ............................................................. 606/116
[58] Field of Search .................... 606/116, 114, 606/164, 264, 167, 159, 170, 96, 223, 224, 225, 104, 180; 81/3.45; 52/157; 604/164, 264

[56] References Cited

U.S. PATENT DOCUMENTS

| | | | |
|---|---|---|---|
| 3,791,387 | 2/1974 | Itoh | 606/114 |
| 4,103,690 | 8/1978 | Harris | 128/418 |
| 4,616,656 | 10/1986 | Nicholson | 128/630 |
| 5,018,530 | 5/1991 | Rank | 128/749 |
| 5,059,197 | 10/1991 | Urie | 606/116 |
| 5,197,482 | 3/1993 | Rank | 128/749 |
| 5,221,269 | 6/1993 | Miller | 604/281 |
| 5,814,052 | 9/1998 | Nakao et al. | 606/114 |

*Primary Examiner*—Michael Buiz
*Assistant Examiner*—Vikki Trinh
*Attorney, Agent, or Firm*—Woodard, Emhardt, Naughton, Moriarty & McNett

[57] ABSTRACT

A lesion localization device and method for localizing lesions are disclosed herein. In the disclosed device, a pair of small diameter shape memory wires are twisted about each other to form an elongate guiding portion extending along a longitudinal axis to an anchoring portion at the distal end of the device. The anchoring portion, which is formed by the distal end portions of the pair of shape memory wires, includes a plurality of loops which radially extend in multiple separate directions away from the longitudinal axis of the device.

20 Claims, 5 Drawing Sheets

LESION LOCALIZATION DEVICE AND METHOD

FIELD OF THE INVENTION

The present invention relates to lesion localization devices and methods, and particularly to devices and methods for localizing pulmonary nodules.

BACKGROUND OF THE INVENTION

When surgery is indicated to remove a lesion in tissue or a biopsy sample is to be obtained, the location of the lesion must first be determined in some manner. With lesions that can be palpated intraoperatively or can be directly visualized, video assisted thoracic surgery is a minimally invasive endoscopic procedure that is preferred over open thoracotomy. With respect to small lesions in certain tissue such as lung tissue, however, it is sometimes difficult for the surgeon to directly localize the lesion to be excised, such as where the lesion is located deep in the pleura or in the posteriomedial aspect of the lung. Further complicating the procedure may be coexisting lung diseases such as pulmonary fibrosis, and the change in geometric relationships caused by the intentional collapse of the lung during the procedure. In these cases, it is usually desirable to mark the lesion with a localizing device of some type.

By one approach for marking lesions in the breast and in the lungs, a wire probe is introduced at the site of the lesion through an introducer needle after the lesion has been located radiographically. The distal end of the probe is typically placed through the lesion, allowing the wire to be braced against the lesion. With conventional localizing wires, however, the wire has a tendency to pull away from the lesion, particularly when the lesion is small or is located in lung tissue which is significantly less dense than breast tissue. Dislodgement of the wire can occur in several ways. For instance, when the patient is transported to surgery the wire may accidentally be pulled out of position as the chest wall and shoulder girdle are moved. The wire may also become dislodged when the lung is deflated prior to removal of the lesion, or when retraction is applied on the wire to tent the lung to allow easier access to the resection site. Some localization wires in the prior art have the further limitation in that they are not repositionable after they have been deployed.

There is a need for a lung lesion localization device that will not dislodge from tissue after deployment, which provides sufficient holding power so that retraction may be applied, and which further allows for repositioning when desired. The present invention addresses this need.

SUMMARY OF THE INVENTION

The present invention relates to a new and useful lesion localization device and method for localizing lesions. In one embodiment of the present invention, there is provided a lesion localization device which is constructed from a pair of small diameter shape memory wires which are twisted about each other to form an elongate portion extending along a longitudinal axis to an anchoring portion at the distal end of the device. The anchoring portion, which is formed by the distal end portions of the pair of shape memory wires, includes a plurality of loops which radially extend in multiple separate directions from the longitudinal axis of the device.

One object of the present invention is to provide a lesion localization device that is advantageous in localizing lesions, including breast and pulmonary lesions.

Yet another object is to provide a lesion localization device that will not dislodge from tissue, can be repositioned when desired, and allows for application of retraction during a surgical procedure.

These and further objects and advantages of the present invention will be apparent from a review of the following specification and claims.

DESCRIPTION OF THE PREFERRED EMBODIMENT

Figure 1:
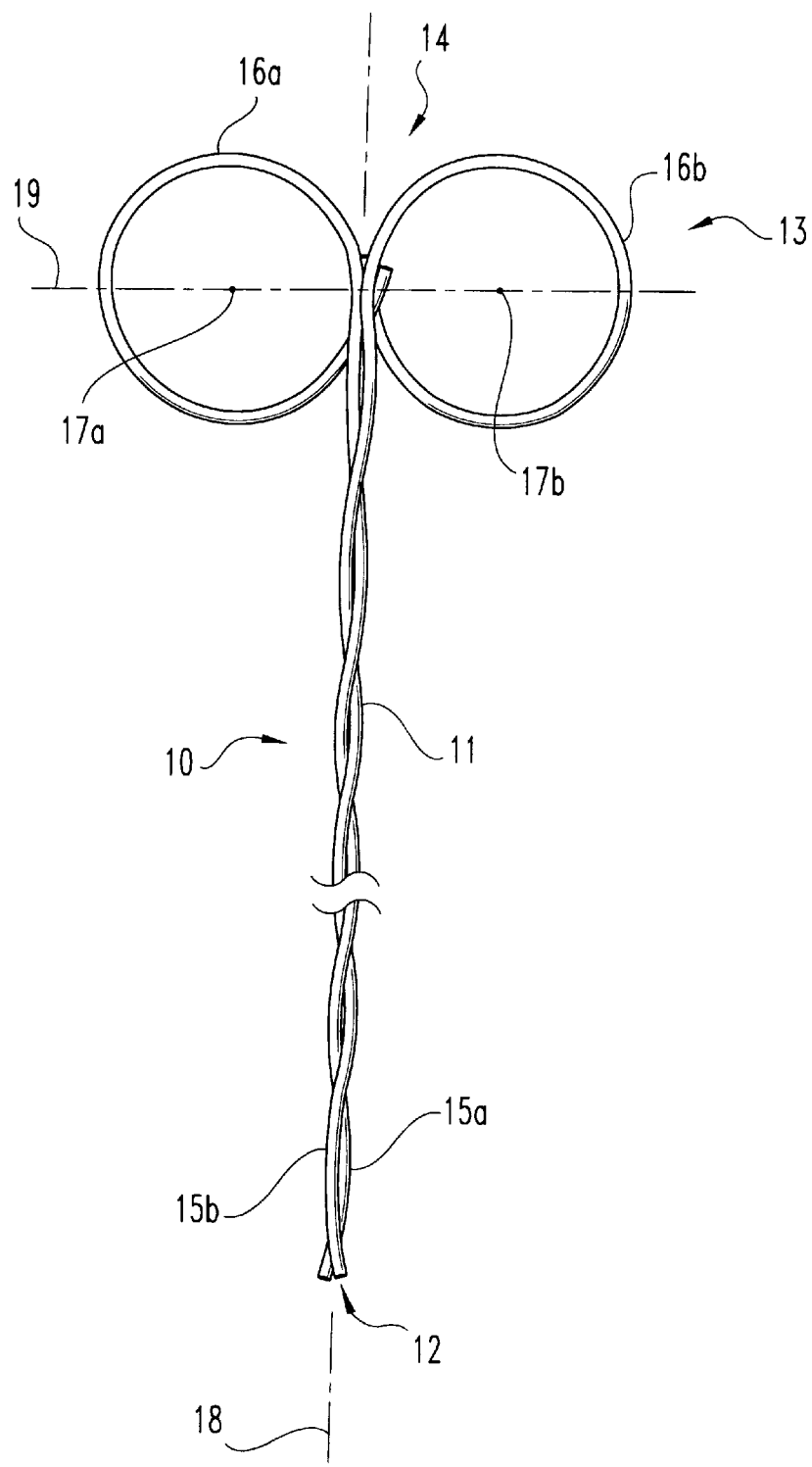
FIG. 1 is a side view of one embodiment of a lesion localization device of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, and any alterations and modifications in the illustrated device, and any further applications of the principles of the invention as illustrated therein are contemplated as would normally occur to one skilled in the art to which the invention relates.

Referring to FIG. 1, lesion localization device 10 includes an elongate guiding portion 11 and anchoring portion 13. Elongate guiding portion 11 extends from a proximal end 12 along and about longitudinal axis 18 to anchoring portion 13 at distal end 14 of localization device 10. Localization device 10 is constructed of two unitary lengths of wire 15a and 15b which are preferably made of a superelastic/shape memory material such as the nickel-titanium alloy known as Nitinol. In one preferred embodiment, wires 15a and 15b are made from polished Nitinol monofilament wire (0.011 in, 0.28 mm).

The shape memory alloy known as Nitinol can be formed into a "remembered" or predisposed shape which it will "remember" even after the material has been substantially deformed away from this shape. When this material is within its superelastic temperature range, it exhibits the property of superelasticity whereby it will allow substantial deformation to occur away from its predisposed shape on the application of external stresses, and will return back to its predisposed shape when the external stresses are removed. At temperatures below this superelastic range, the material will not entirely regain its predisposed shape on the removal of external stress, but will regain the remainder of its predisposed shape upon heating back into the material's superelastic temperature range. At still lower temperatures, the material will stay deformed after stress on it has been released, but will resume its remembered predisposed shape when heated back into its superelastic temperature range. For the present invention, the material to be selected for wire 15 is preferably in its superelastic temperature range at body temperature (37° C.) or is at least substantially superelastic at this temperature.

In the embodiment shown in FIG. 1, wires 15a and 15b are twisted or braided about each other along their proximal length, and are preferably held together near proximal end 12 by an adhesive or glue. Anchoring portion 13 of localization device 10 is formed at the distal portion of wires 15a and 15b, which are pre-shaped into two opposing loops 16a and 16b respectively. In the embodiment depicted in FIG. 1, loops 16a and 16b are circularly-shaped, respectively defining central axes 17a and 17b that are each perpendicular to a diameter of each respective loop and that pass through the center of the defining loop. In this embodiment, each loop 16a and 16b includes a length of wire that makes a 360° path about its respective central axis. Loops 16a and 16b may each have the same diameter or may individually have different diameters. The preferred diameter of loops 16a and 16b is about 5 mm. as measured when lesion localization device 10 is in its unrestrained, superelastic state. In the embodiment shown in FIG. 1, each of loops 16a and 16b lie in a plane which radially extends from longitudinal axis 18. It can be seen that central axes 17a and 17b are perpendicular to a transverse axis 19 that is generally perpendicular to longitudinal axis 18 of lesion localization device 10. Anchoring portion 13 thus forms the shape of a figure eight. As shown in FIG. 1, loops 16a and 16b are oppositely disposed relative to each other along transverse axis 19.

Figure 2:
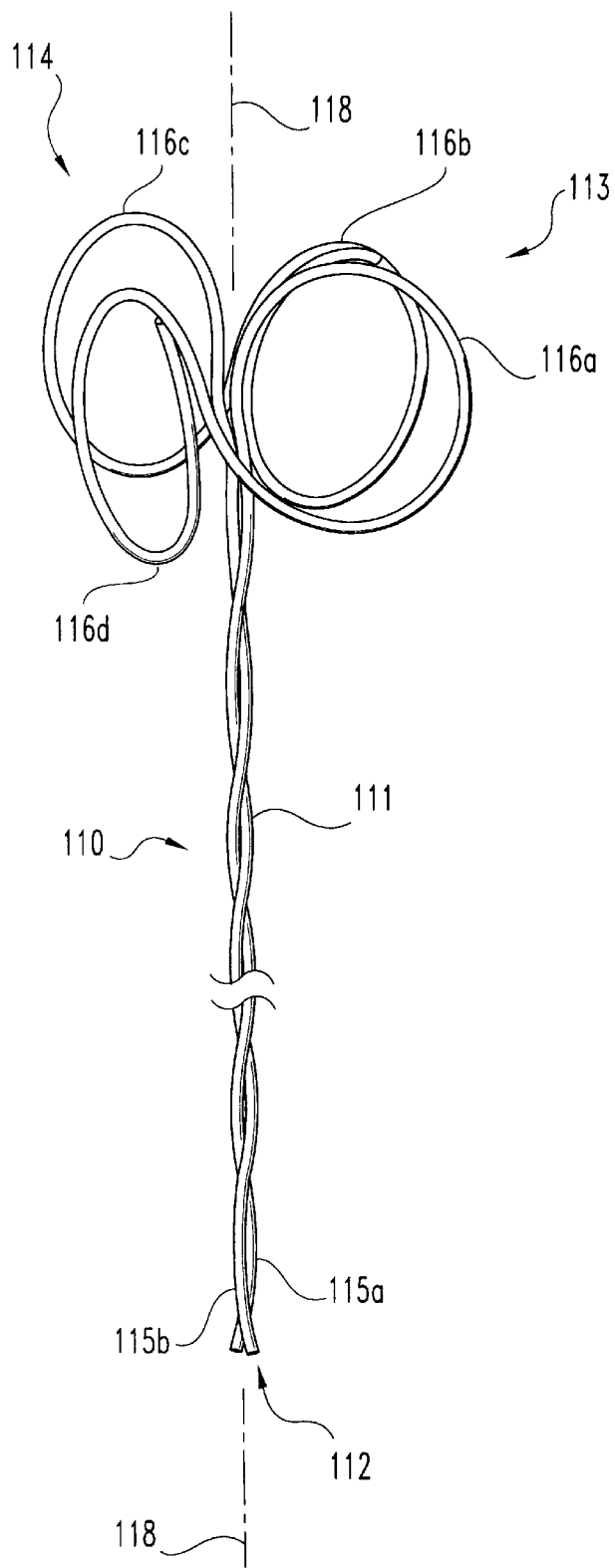
FIG. 2 is a side view of another embodiment of a lesion localization device of the present invention.

FIG. 2 depicts a second preferred embodiment in which anchoring portion 113 of lesion localization device 110 incorporates a set of four loops 116a–116d. In this embodiment, each of wires 115a and 115b form two opposing loops, with loops 116a and 116d being formed from wire 115a and loops 116b and 116c being formed from wire 115b.

Figure 3:
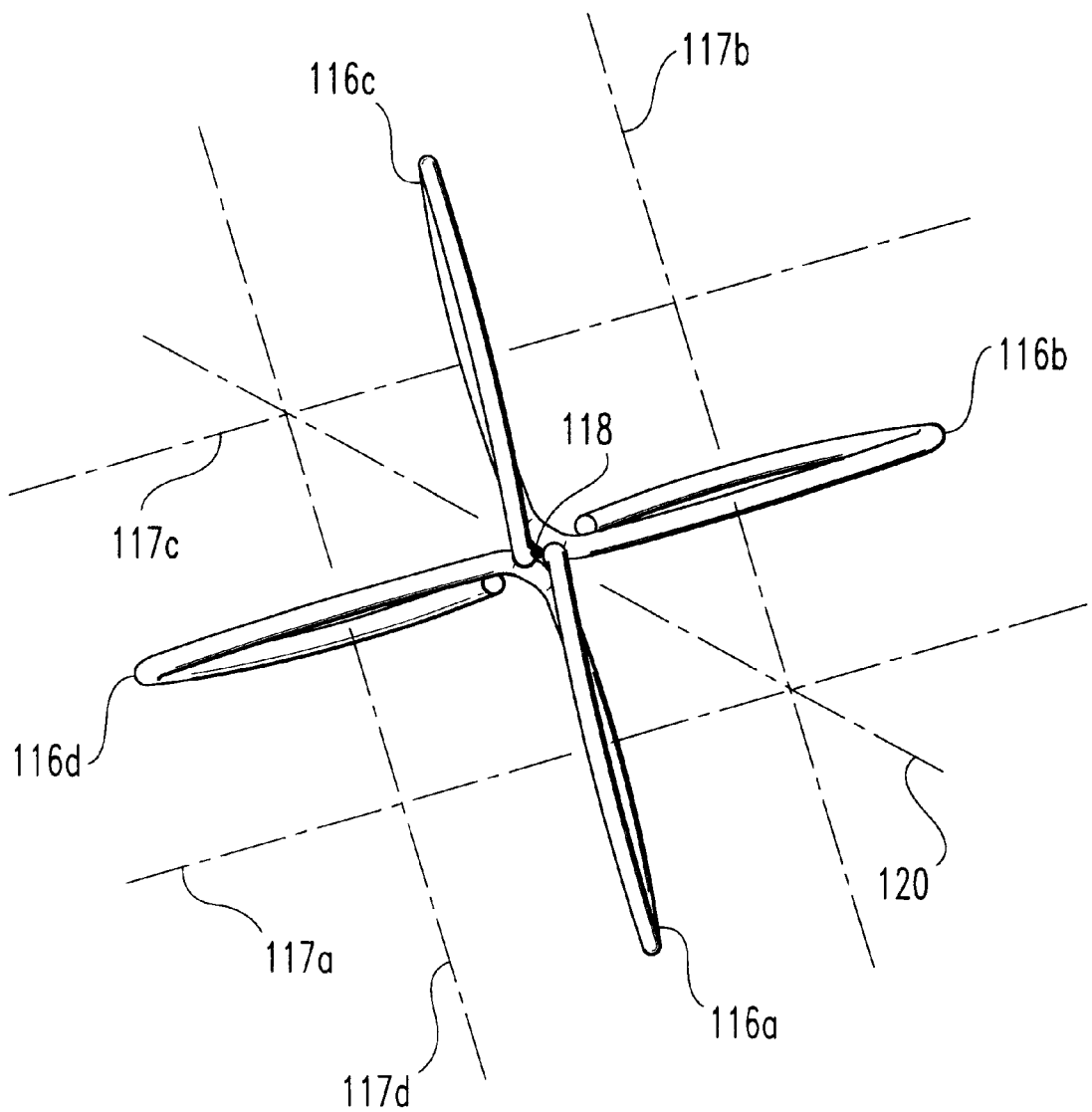
FIG. 3 is a top view of the embodiment shown in FIG. 2.

FIG. 3 shows a top view of anchoring portion 113 of lesion localization device 110 shown in FIG. 2. Loops 116a–116d are oppositely disposed about transverse axis 120 which is perpendicular to longitudinal axis 118. Loops 116b and 116d form a set of loops that generally lie in a plane intersecting longitudinal axis 118 and radially extend from longitudinal axis 118. Loops 116a and 116c form a second set of loops that also lie in a plane intersecting longitudinal axis 118 and radially extend from longitudinal axis 118. Loops 116a and 116c lie generally in a common plane which is perpendicular to the general plane containing loops 116b and 116d. Loops 116a–d each respectively close about themselves along adjacent transverse sections, as shown in FIGS. 2 and 3, wherein it is seen that each loop is positioned slightly out of line with the axis of tension when device 110 is pulled along longitudinal axis 118.

FIG. 3 also depicts central axes 117a–d for each of loop 116a–d respectively, which are each perpendicular to the central axes of each neighboring loop relative thereto. That is, central axes 117a and 117c of loops 116a and 116c are perpendicular to central axes 117b and 117d of neighboring loops 116b and 116d.

Figure 4:
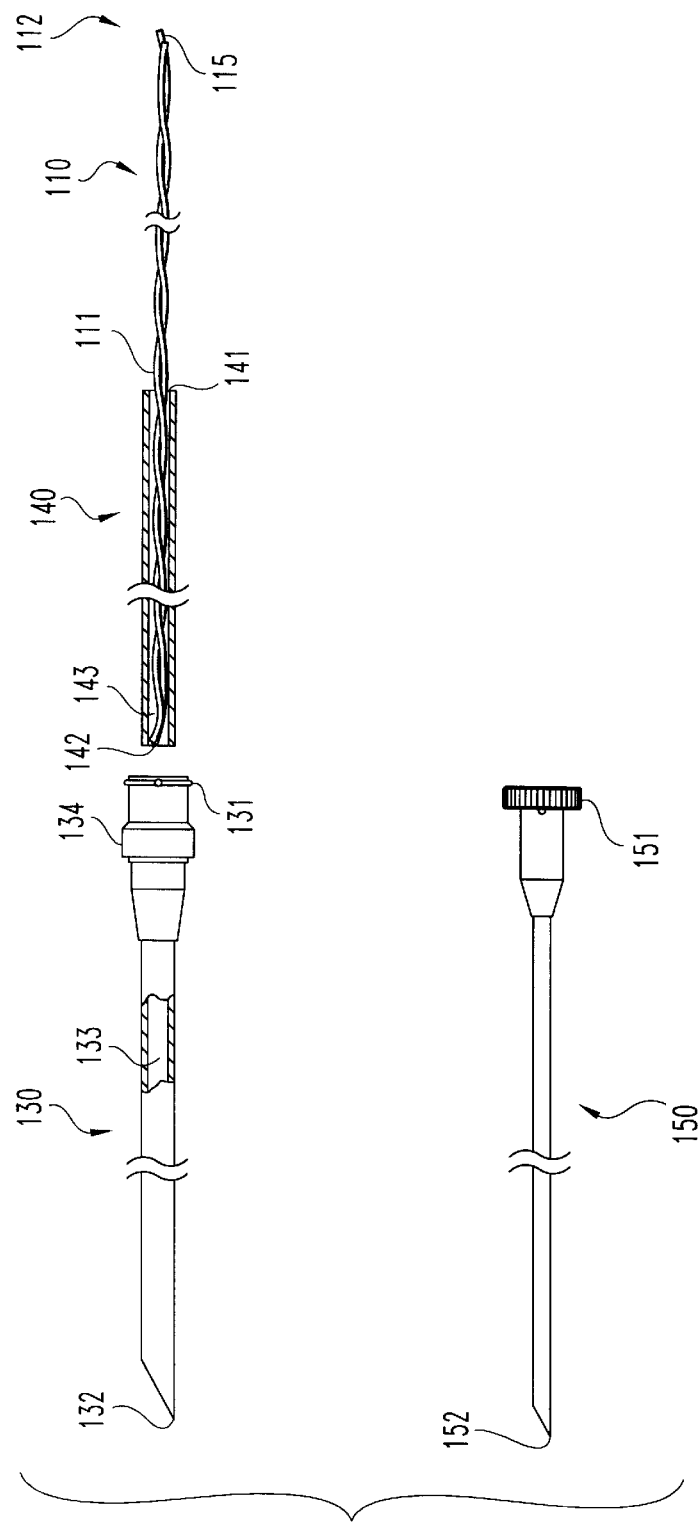
FIG. 4 is a side view of introducer needle 130, stylet 150, and insertion device 140 with lesion localization device 110 loaded in the lumen of insertion device 140.

Referring to FIG. 4, there is shown an introducer needle 130 having a proximal end 131 and a distal end 132. A female luer-lock connector hub 134 is located at proximal end 131 of introducer needle 130 and is adapted for receiving insertion device 140, also depicted in FIG. 4. Introducer needle 130 further defines lumen 133 that extends longitudinally from proximal end 131 to distal end 132. Distal end 132 of introducer needle 130 has a sharp edge for piercing and penetrating tissue to the lesion site. Introducer needle 130 may suitably be a standard biopsy needle, such as a 20 gauge Chiba biopsy needle obtained from Becton Dickinson, Rutherford, N.J. The needle assembly further includes stylet 150 which is withdrawn from the needle after localizing the needle in the body and prior to inserting lesion localization device 110.

FIG. 4 also shows insertion device 140 receivable in hub 134 of introducer needle 130. Insertion device 140 defines a lumen 143 that extends longitudinally from a proximal end 141 to a distal end 142. Lumen 143 is adapted to receive lesion localization device 110. Both ends of insertion device 140 are preferably burnished. Insertion device 140 may suitably be made from standard 20 gauge needle stock with a length of about 3 inches (7.6 cm).

Insertion device 140 may be used in a pulmonary lesion localization procedure to introduce lesion localization device 110 into lumen 133 of introducer needle 130. In a nonpulmonary lesion localization procedure, lesion localization device 110 may sometimes be directly loaded into lumen 133 of introducer needle 130 by placing proximal end 112 of elongate guiding portion 111 into lumen 133 of introducer needle 130 at distal end 132 and retracting lesion localization device 110 towards proximal end 131 of introducer needle 130. Lesion localization device 110 is retracted through lumen 133 of introducer needle 130 until anchoring portion 113 is within lumen 133 in an unwound state.

Figure 5:
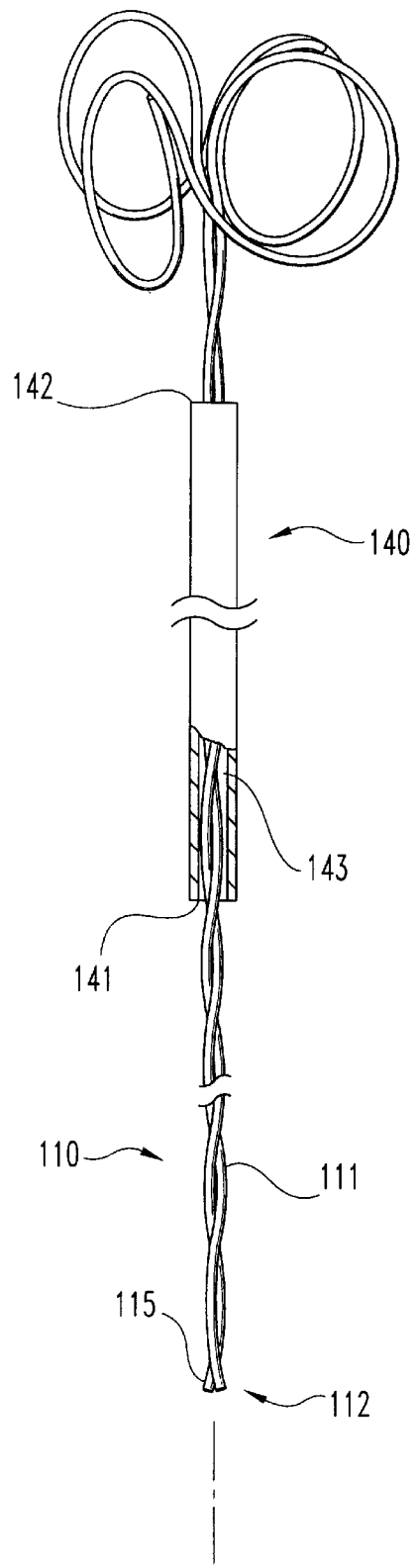
FIG. 5 depicts a lesion localization device of the present invention being loaded into insertion device 140.

Referring to FIG. 5, lesion localization device 110 may be loaded into insertion device 140 by placing proximal end 112 of elongate portion 111 into lumen 143 of insertion device 140 at distal end 142 and retracting lesion localization device 110 towards proximal end 141. Lesion localization device 110 is retracted through lumen 143 of insertion device 140 until anchoring portion 113 is within insertion device 140 in an unwound state.

In one method of localizing a lesion of the present invention, the lesion in question is initially visualized radiographically such as by thin section computer tomography. Lesion localization device 110 is loaded within lumen 133 of introducer needle 130 prior to advancing distal end 132 of introducer needle 130 to a predetermined location, preferably on the opposite side of the lesion from the insertion site. Introducer needle 130 is preferably passed through the lesion. Lesion localization device 110 is advanced towards distal end 132 of introducer needle 130 until anchoring portion 113 is no longer restrained by introducer needle 130. Friction may be felt within lumen 133 of introducer needle 30 as lesion localization device 110 is advanced and no further friction is felt when anchoring portion 113 emerges from distal end 132 of introducer needle 130. After anchoring portion 113 emerges from distal end 132 of introducer needle 130, anchoring portion 113 regains its predisposed multiple loop configuration.

When localizing a lesion within the lungs, stylet 150 may be placed within lumen 133 of introducer needle 130 prior to advancing the introducer needle to the predetermined location. After advancing introducer needle 130 to a predetermined location and prior to inserting lesion localization device 110 into lumen 133 of introducer needle 130, stylet 150 is removed from introducer needle 130. Lesion localization device 110 is loaded into insertion device 140 as described above with reference to FIG. 5. Distal end 142 of insertion device 140 is then inserted into hub 134 of introducer needle 130 so that lumen 143 of insertion device 140 and lumen 133 of introducer needle 130 are substantially aligned. Lesion localization device 110 is then advanced towards distal end 132 of introducer needle 130 as described above.

After anchoring portion 113 of localization device 110 has emerged from distal end 132 of introducer needle 130, the positioning of localization device 110 is preferably confirmed prior to removal of introducer needle 130. Confirmation may be accomplished with a radiographic method such as by thin section computer tomography. If desired, localization device 110 can be pulled back into introducer needle 130 and introducer needle 130 can be repositioned for replacement of device 110. The portion of elongate guiding portion 113 of lesion localization device 110 that is external to the body may then be loosely coiled on the patient's chest, draped with sterile covers, and the patient may then be escorted to the preoperative holding area.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A lesion localization device comprising an elongate guiding portion extending from a proximal end along a longitudinal axis to an anchoring portion at a distal end opposite said proximal end, said guiding portion being configured for guiding said anchoring portion to said lesion, said anchoring portion including at least two loops, said loops radially extending in separate directions from said longitudinal axis and being made from a shape memory material.

2. The lesion localization device of claim 1, wherein said anchoring portion includes two loops in the combined shape of a figure eight.

3. The lesion localization device of claim 1, wherein said loops are oppositely disposed about a transverse axis generally perpendicular to said longitudinal axis of said lesion localization device.

4. The lesion localization device of claim 1, wherein said anchoring portion includes four loops.

5. The lesion localization device of claim 4, wherein each of said loops define a substantially circular shape.

6. The lesion localization device of claim 5, wherein said anchoring portion includes a first set of two opposing loops and a second set of two opposing loops wherein said loops in each set oppose each other by an angle of about 180 degrees, said first and second sets of two opposing loops being disposed such that each loop of said first set is opposed to a loop in said second set by an angle of about 90 degrees.

7. A lesion localization device comprising a pair of wires, said wires having a proximal end opposite a distal end, said pair of wires being twisted around each other to form an elongate portion, said elongate portion extending from said proximal end along a longitudinal axis to a looped portion and configured for guiding said looped portion to said lesion, said looped portion including a plurality of loops radially extending from said longitudinal axis, a first one of said loops being formed from a first one of said pair of wires and a second one of said loops being formed from a second one of said pair of wires, said wire loops being made from a shape memory material.

8. The lesion localization device of claim 7, wherein said looped portion includes two loops in the combined shape of a figure eight.

9. The lesion localization device of claim 8, wherein said loops are oppositely disposed about a transverse axis generally perpendicular to said longitudinal axis.

10. A method of localizing a lesion, said method comprising:
   a) localizing said lesion;
   b) providing an introducer needle having a proximal end and a distal end, said distal end having a hub;
   c) advancing the distal end of the introducer needle to a predetermined location;
   d) providing an insertion device having a proximal end, a distal end and a lumen, and a lesion localization device including an elongate guiding portion extending from a proximal end along a longitudinal axis to an anchoring portion at the distal end thereof, the guiding portion being configured for guiding the anchoring portion to the lesion, the anchoring portion including at least two loops, the loops radially extending from said longitudinal axis;
   e) loading the lesion localization device into the lumen of the insertion device;
   f) placing the proximal end of the insertion device into the hub of the introducer needle;
   g) advancing the lesion localization device through the lumen of the introducer needle towards the distal end of the introducer needle until the anchoring portion of the lesion localization device is no longer restrained by the introducer needle; and
   h) confirming the lesion localization device is in the predetermined location prior to removing the introducer needle.

11. The method of claim 10, including withdrawing the lesion localization device into the introducer needle after the anchoring portion of the lesion localization device is no longer restrained by the introducer needle and repositioning the introducer needle.

12. The method of claim 10, including repositioning the introducer needle prior to advancing the localization device.

13. The method of claim 10, wherein the loading of the lesion localization device into the lumen of the insertion device includes inserting the proximal end of the elongate guiding portion of the lesion localization device into the lumen of the insertion device at the distal end of the insertion device and advancing the proximal end of the elongate portion towards the proximal end of the insertion device.

14. The method of claim 10, wherein the anchoring portion is made from a shape memory material.

15. A method of localizing a lesion, the method comprising:
   a) localizing the lesion;
   b) loading an introducer needle having a proximal end, a distal end and a lumen with a lesion localization device, said device including an elongate guiding portion extending from a proximal end along a longitudinal axis to an anchoring portion at a distal end thereof, the guiding portion being configured for guiding the anchoring portion to the lesion, the anchoring portion including at least two loops, the loops radially extending from the longitudinal axis;
   c) advancing the distal end of the introducer needle to a predetermined location;
   d) advancing the localization device through the lumen of the introducer needle towards the distal end of the introducer needle until the anchoring portion of the lesion localization device is no longer restrained by the introducer needle; and
   e) confirming the lesion localization device is in the predetermined location prior to removing the introducer needle.

16. The method of claim 15, including withdrawing the lesion localization device into the introducer needle after the anchoring portion of the lesion localization device is no longer restrained by the introducer needle, and repositioning the introducer needle.

17. The method of claim 15, including repositioning the introducer needle prior to advancing the lesion localization device.

18. The method of claim 15, wherein the loading an introducer needle includes inserting the proximal end of the elongate guiding portion of the lesion localization device into the lumen of the introducer needle at the distal end of the introducer needle and advancing the proximal end of the elongate guiding portion towards the proximal end of the introducer needle.

19. The method of claim 15, wherein the anchoring portion is made from a shape memory material.

20. A kit for lesion localization, comprising:
   a) a lesion localization device including an elongate guiding portion extending from a proximal end along a longitudinal axis to an anchoring portion at a distal end opposite said proximal end, said guiding portion being configured for guiding said anchoring portion to the lesion, said anchoring portion including at least two loops, said loops radially extending from said longitudinal axis and being made from a shape memory material;
   b) an introducer needle having a lumen adapted for receiving the lesion localization device; and
   c) an insertion device for introducing said lesion localization device into said lumen of said introducer needle, said insertion device having a lumen adapted to receive said localization device.

* * * * *